United States Patent [19]

Durr et al.

[11] Patent Number: 5,670,536

[45] Date of Patent: Sep. 23, 1997

[54] PHARMACEUTICAL COMPOSITION BASED ON TAXOIDS

[75] Inventors: Manfred Durr, Bergheim-Glessen; Jörg-Christian Hager; Armin Wendel, both of Cologne, all of Germany

[73] Assignee: Rhone-Poulenc Rorer S.A., Antony, France

[21] Appl. No.: 428,261

[22] Filed: Apr. 25, 1995

[30] Foreign Application Priority Data

Apr. 25, 1994 [FR] France .................................. 94 04951

[51] Int. Cl.$^6$ .................................................. A61K 9/127
[52] U.S. Cl. .................................... 514/449; 549/510
[58] Field of Search ................................ 549/510, 511; 514/449

[56] References Cited

U.S. PATENT DOCUMENTS

| | | | |
|---|---|---|---|
| 4,507,217 | 3/1985 | Sears | 252/62.54 |
| 4,534,899 | 8/1985 | Sears | 260/403 |
| 5,415,869 | 5/1995 | Straubinger et al. | |
| 5,484,809 | 1/1996 | Hostetler et al. | 514/449 |

FOREIGN PATENT DOCUMENTS

| | | |
|---|---|---|
| 0 118 316 | 9/1984 | European Pat. Off. |
| WO 93/18751 | 9/1993 | WIPO. |
| WO 94/26253 | 11/1994 | WIPO. |
| WO 94/26254 | 11/1994 | WIPO. |

*Primary Examiner*—James H. Reamer
*Attorney, Agent, or Firm*—Finnegan, Henderson, Farabow, Garrett & Dunner, L.L.P.

[57] ABSTRACT

This invention relates to a pharmaceutical composition comprising as active principle, docetaxel or a taxoid derived from docetaxel, one or more unsaturated phospholipids and a small amount of one or more negative phospholipids, allow the active principle to be formulated in high concentration and are suitable for administration by injection.

33 Claims, No Drawings

PHARMACEUTICAL COMPOSITION BASED ON TAXOIDS

FIELD OF THE INVENTION

The present invention relates to a pharmaceutical composition for administration by injection, comprising a therapeutic antitumor agent of the taxoid class.

BACKGROUND OF THE INVENTION

Active principles of the taxoid class are injectable, but their solubility in water is especially low. This makes it very difficult to produce a preparation for parenteral administration which is acceptable from a therapeutic standpoint.

The taxoid class more especially includes Taxotere (docetaxel) as well as derivatives of this product.

Among docetaxel derivatives, there may be mentioned, in particular, the products of formula:

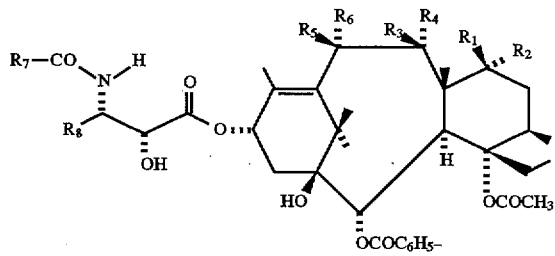

in which:

$R_1$ and $R_2$ each represent a hydrogen atom, or alternatively one of $R_1$ and $R_2$ represents a hydrogen atom and the other represents a hydroxyl, acyloxy or acylcarbonyloxy radical, or alternatively $R_2$ represents a hydrogen atom and $R_1$ forms a bond with the carbon atom of the methyl radical at the α-position so as to form a cyclopropane ring, one of $R_3$ and $R_4$ represents a hydrogen atom and the other represents a hydroxyl radical, or alternatively $R_3$ and $R_4$ together form an oxo radical, $R_5$ and $R_6$ each represent a hydrogen atom, or alternatively one of $R_5$ and $R_6$ represents a hydrogen atom and the other represents a hydroxyl, acyloxy, acylcarbonyloxy or alkoxymethylcarbonyloxy radical, or alternatively $R_5$ and $R_6$ together form an oxo radical, $R_7$ represents an alkoxy, alkenyloxy or cycloalkyloxy radical, and $R_8$ represents an alkyl, straight or branched-chain alkenyl or alkynyl radical or a cycloalkyl radical containing 3 or 6 carbon atoms, or alternatively $R_8$ represents a phenyl radical unsubstituted or substituted with one or more identical or different atoms or radicals chosen from halogen atoms and alkyl, alkoxy, dialkylamino, acylamino, alkoxycarbonylamino and trifluoromethyl radicals, or a 5-membered aromatic heterocyclic radical containing one or more identical or different hetero atoms chosen from nitrogen, oxygen and sulphur atoms, the alkyl radicals and the alkyl portions of other radicals containing 1 to 8 carbon atoms in a straight or branched-chain, and the alkenyl or alkynyl radicals containing 2 to 8 carbon atoms.

Preferably, the taxoids which may be used in the present invention are the derivatives mentioned above in which, with $R_2$ representing a hydrogen atom, $R_1$ represents a hydrogen atom or a hydroxyl radical, or alternatively $R_1$ forms a single bond with the carbon atom of the methyl radical at the α-position, $R_3$ and $R_4$ together form an oxo radical, $R_5$ represents a hydrogen atom and $R_6$ represents a hydrogen atom or a hydroxyl, acetyloxy or methoxyacetyloxy radical, or alternatively $R_5$ and $R_6$ together form an oxo radical, $R_7$ represents a t-butoxy radical and $R_8$ represents an isobutyl, isobutanyl, butenyl, cyclohexyl, phenyl, 2-furyl, 3-furyl, 2-thienyl, 3-thienyl, 2-thiazolyl, 4-thiazolyl or 5-thiazolyl radical.

The taxoid derivatives may be obtained, in particular, according to or by analogy with the methods described in WO 92/09589, WO 93/06093, EP 534,708, EP 558,959 and FR 2,697,019, or according to or by analogy with the method described in the examples.

Hitherto, different formulations of taxoid derivatives have been developed, such as, in particular, compositions based on a surfactant and ethanol. Ethanol is the best pharmaceutical solvent of the compounds of the taxoid class.

As an example, according to the publication of Rowinsky, Lorraine, Cazenave and Donehower, Journal of the National Cancer Institute, 82(15), 1247–1259 (1990), a primary solution is prepared, termed "stock solution", containing approximately 6 mg/ml of Taxol in a solvent mixture composed of:

50% by volume of ethanol
50% by volume of Cremophor EL.

On injection, this solution is mixed with a perfusion fluid containing sodium chloride or dextrose. To obtain a mixture which is stable from both a physical standpoint and a chemical standpoint, it is necessary, according to this publication, to limit the concentration of active principle in the perfusion solution to concentrations not exceeding 0.6 mg/ml (see page 1251 column 1, 3rd paragraph).

It is nevertheless desirable to be able to inject sufficiently large doses of active principle: generally, clinicians like to be able to inject concentrations or active principle of between approximately 0.3 and 1 mg/ml in the perfusion fluid. Unfortunately, the limiting factor is very often linked to the excipient content of the composition. At doses higher than those mentioned above, anaphylactic shock phenomena may occur which are difficult to control, due for the most part to the Cremophor (Rowinsky et al., J. Nat. Cancer Inst., 82(15), 1250 (1990), 2nd column, last paragraph; Cancer Treat. Report., 71, 1171–1184 (1987)).

According to the above publication, to obtain such concentrations (ranging up to 1 mg/ml), it is necessary to inject solutions of active principle containing concentrations of ethanol, and most particularly Cremophor, of approximately 8 g per 100 ml of perfusion solution. However, since treatment often requires the administration of high doses of active principle, and the solubility of the active principle in the solution is relatively low, the injection of large volumes is required. This has the effect of causing symptoms of alcoholism during treatment, in addition to the anaphylactic symptoms.

Various investigations have been carried out with the aim of preparing compositions for parenteral administration of water-insoluble active principles, in particular on the basis of phospholipids (EP 118,316). However, inasmuch as different types of active principle were involved, the problem to be solved was not that of being able to increase the concentrations of active principle to high concentrations in solutions intended for injection. Consequently, these methods did not solve the problem of the preparation of an improved injectable composition having a sufficient titer of active principle for a product of the taxoid class.

DESCRIPTION OF THE INVENTION

It has now been found that the anticancer agent docetaxel and taxoid derivative of docetaxel can be formulated at exceptionally high levels as a stable pharmaceutical composition not displaying an intolerance problem. The pharmaceutical compositions according to the invention comprise as active principle docetaxel or a taxoid derived from docetaxel, one or more unsaturated phospholipids and a small amount of one or more negative phospholipids. Preferably, the pharmaceutical compositions according to the invention comprise 3 to 15 mg/ml of active principle.

The compositions according to the invention can be liquid, frozen or lyophilized. The liquid compositions are clear, stable solutions in which no crystals are observed. The frozen or lyophilized compositions are more suitable for storage, and also enable clear, stable solutions with a high concentration of active principle to be reconstituted.

The term "stable solution" means a solution which is stable at room temperature and in which no particles of active principle appear for up to 8 weeks and possibly up to 8 months.

The lyophilized compositions are a preferred aspect of the invention. They have the advantage of good physical and chemical stability, and make it possible, most particularly, to increase the content of active principle in the injectable compositions without giving rise, as a result, to the problems of intolerance previously observed. It is thus possible, by application of the present invention, to enhance very greatly the solubility of the anticancer agent docetaxel and taxoids derived from docetaxel, and to produce injectable compositions in which the relative proportion of the active principle with respect to the excipients is greatly increased.

As a result, it is now possible to remedy the drawbacks linked to the presence of excipients whose toxicity is significant at high contents.

According to the invention, the unsaturated phospholipids are chosen from natural, synthetic or semi-synthetic phospholipids; in particular, natural phospholipids such as phospholipids of vegetable origin (especially rapeseed, sunflower or soya-bean lecithins, and, for example, lecithins, composed of different phospholipids in varying proportions) or of animal origin (especially egg-yolk lecithin).

As an example, there may be mentioned, in particular, natural phosphatidylcholines such as, in particular, the Phospholipons°: Phospholipon 80°, Phospholipon 90°, Phospholipon 100°. Phosphatidylethanolamines, phosphatidylinositols, phosphatidylserines, phosphatidylglycerols; phosphatidic acid, or mixtures of these phospholipids, may also be mentioned. It is understood that the preferred phospholipids are phospholipids of a good grade of purity, that is to say having a purity of more than 90%.

The unsaturated synthetic phospholipids can be, for example, phospholipids of the structure:

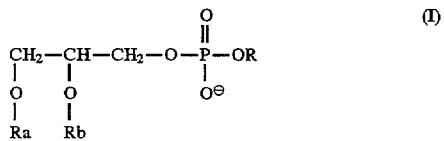

(I)

in which R is an alkyl radical substituted with amino or with trialkylammonio (the alkyl radicals containing 1 to 4 carbon atoms), and $R_a$ and $R_b$ are hydrogen atoms or saturated or unsaturated acyl residues of $C_0$ to $C_{22}$ fatty chains and are identical or different, provided that at least one is an unsaturated radical.

As an example, preference is given more especially to unsaturated phospholipids in which R is aminoethyl or trimethylammonioethyl, and phospholipids in which $R_a$ and/or $R_b$ are palmitoyl, stearoyl, myristoyl, oleoyl, linoleoyl, or linolenoyl, at least one being unsaturated; and phosphatidylcholine derivatives in particular.

The Phospholipons are natural phospholipids of vegetable origin extracted from soya-bean lecithin, which contain a level of unsaturated acyl chains of greater than 70%.

According to the invention, the negative phospholipids are chosen from natural or synthetic anionic substances such as, for example, the alkali metal salts or quaternary ammonium salts of phosphatidylglycerol, of phosphatidylserine, of phosphatidylinositol, of phosphatidic acid or their derivatives.

The alkali metal salts of anionic phospholipids are, in particular, the sodium or potassium salts.

The anionic substances of natural origin originate more especially from sunflower or soya bean.

Among anionic substances, preference is given more especially to the salts of soya-bean phosphatidylglycerol, dimyristoylphosphatidylglycerol or dipalmitoylphosphatidylglycerol, or their derivatives.

The preparation of the composition according to the invention has the considerable advantage of not involving an organic solvent which is toxic from a pharmaceutical standpoint (such as, for example, chlorinated solvents) and whose removal might not be complete in the final composition.

According to the invention, a homogeneous dispersion is formed by dissolution of one or more unsaturated phospholipids, a small amount of one or more negative phospholipids and an active principle, which is docetaxel or a taxoid derived from docetaxel, in an alcohol (preferably ethanol), followed by evaporation of all or part of the alcohol until a gel or a viscous liquid is obtained, which gel or liquid is taken up by adding water with stirring and then homogenization. The homogeneous dispersion thereby obtained may be frozen or lyophilized.

It is understood that the homogenization may be carried out in several repeated steps.

The homogeneous dispersion thereby obtained is stable and clear. It is an advantage that the dispersion comprises particles containing active principle, said particles being of only very small size, and can be subjected to sterilizing filtration. On average the diameter of particles containing active principle in the dispersion is usually less than 200 nm, preferably on average less than 100 nm. It is understood that such homogeneous dispersions fall within the scope of the present invention.

The lyophilizates obtained may be solubilized immediately before administration in an injectable medium at the time of use.

When homogeneous dispersion prepared is subjected beforehand to a sterilizing filtration, filtration is usually performed using a 0.40 to 0.10 µm, and preferably 0.30 µm to 0.20 µm, filter, and more especially using a 0.22 µm filter.

The evaporation step is preferably carried out under an inert atmosphere, for example under nitrogen or under argon, at a temperature below 45° C. and preferably at a temperature below 30° C. It is advantageous to work under reduced pressure. It is not always essential to remove the alcohol completely before adding water, it being possible for a residue of alcohol to be removed subsequently after the formation of the dispersion.

The aqueous solution can optionally comprise, in addition, additives. Nonionic compounds such as, for example, a cryoprotective agent intended for preventing the reprecipitation of the active principle and/or an agent intended for adjusting the isotonicity of the final solution to be injected, can, in particular, be added to the medium.

These agents can be chosen from sugars (for example glucose, maltose, lactose, mannitol, sorbitol), polymers [for example dextran (dextran 1500, dextran 40000), injectable polyvinylpyrrolidones, polyethylene glycol, etc.], amino acids (for example glycine) or any other agent capable of exercising this function. It can also contain one (or more) preservative(s). The additives may be added during different steps of the preparation, however it is advantageous to add them to the homogeneous dispersion.

Freezing may be performed according to customary techniques, and optionally in an accelerated manner.

The lyophilization is also performed according to customary techniques.

The concentration of active principle in the pharmaceutical composition according to the invention is typically between 3 and 15 mg/ml, without the appearance of any particles of active principle. Preferably, the composition contains from5 mg/ml to values above 10 mg/ml of active principle, for example from 5 to 15 mg/ml of active principle.

The active principle introduced into the composition represents 1 to 30% by weight relative to the total weight of the phospholipids introduced. Preferably, the active principle represents 3 to 20%, and more especially 3.5 to 10% by weight relative to the total weight of the phospholipids.

The unsaturated phospholipid(s) is/are preferably derived from phosphatidylcholine. According to a preferred aspect of the invention, phosphatidylcholine constitutes from 70 to 100% of the unsaturated phospholipid introduced.

The negative phospholipid is introduced in small amounts. Generally speaking, it is advantageous to introduce it in a proportion of 0.1 to 4%, preferably 0.4 to 0.8% and more especially approximately 0.5% by weight relative to the total weight of unsaturated phospholipid(s).

When the composition obtained is lyophilized, it may be redissolved at the time of use in any compatible and pharmaceutically acceptable injectable medium. The lyophilizate may be advantageously taken up with injection grade double-distilled water, in a volume equivalent to the initial volume of the solution to be lyophilized. When the solution has been frozen (for example frozen bag), it can be thawed at the time of use.

The solutions thereby obtained have the advantage of being stable and of containing a high level of active principle without any precipitation or crystallization occurring. In another alternative, the lyophilizate can also be redissolved beforehand, and the solution stored until the time of use. The volume of injectable medium added to the said composition is preferably identical to the initial volume of the composition previously subjected to lyophilization. When the solution has been frozen, it may also be stored after thawing until used.

EXAMPLES

The examples which follow illustrate the present invention.

Example 1

1.0 g of docetaxel (Taxotere), 10.0 g of Phospholipon 90 and 0.05 g of phosphatidyl glycerol sodium salt are dissolved in 90 ml of ethanol and then stirred until dissolution is complete. The ethanol is evaporated off under an inert atmosphere (nitrogen) and under a reduced pressure of 0.5 kPa at a temperature below 30° C. until an ethanol-free pasty solid is obtained. After the addition of water to a volume of 50.0 ml and dispersion of the mixture by stirring, a dispersion of milky appearance is first obtained, which is homogenized until a clear, fine dispersion is obtained, to which 50 ml of an aqueous solution containing 30.0 g of maltose are added with stirring. The dispersion thereby obtained is subjected to a sterilizing filtration using a 0.22 µm filter.

The sterile dispersion is divided into 10-ml fractions in 20-ml vials and then lyophilized.

After the lyophilizate has been taken up with 10 ml of double-distilled water for injections, a clear, stable solution is obtained immediately 80% transparency measured using a photometer at 660 nm).

Example 2

The procedure is as above in Example 1, but starting from 0.1 g of docetaxel, 2.0 g of Phospholipon 90 and 0.01 of phosphatidyl glycerol sodium salt. After the addition of water to a volume of 16.7 ml, dispersion of the mixture by stirring and homogenization, a clear dispersion is obtained, to which 3.3 ml of an aqueous solution containing 2.0 g of maltose is added and which is then subjected to a sterile filtration.

The clear dispersion is divided into 4-ml fractions in 10ml vials and then lyophilized.

A lyophilizate is obtained, from which it is possible to reconstitute a perfectly clear and stable solution after adding 4 ml of water containing 0.9% of sodium chloride.

Stability measurements show that the solution is still clear after more than 8 weeks at a temperature of 20° C.

The particle diameter is approximately 47 nm.

Example 3

The procedure is as above in Example1, but starting from0.1 g of docetaxel, 1.5 g of Phospholipon 90° and 0.075 g of phosphatidyl glycerol sodium salt. After the addition of water to a volume of 12.5 ml, dispersion of the mixture by stirring and homogenization, a clear dispersion is obtained, to which 2.5 ml of an aqueous solution containing 1.5 g of maltose are added and which is then subjected to a sterile filtration.

The clear dispersion is divided into 1.5-ml fractions in 5-ml vials and then lyophilized.

A lyophilizate is obtained, from which it is possible to reconstitute a perfectly clear and stable solution after adding 1.5 ml of water containing 0.9% of sodium chloride.

Stability measurements show that the solution is still clear after more than 8 weeks at a temperature of 20°0 C.

The particle diameter is approximately 71 nm.

Example 4

The procedure is as above in Example 1, but starting from 0.1 g of docetaxel, 2.0 g of Phospholipon 90° and 0.01 g of phosphatidyl glycerol sodium salt. The ethanol is evaporated off under an inert atmosphere and under a reduced pressure of 0.15 kPa at a temperature below 30° C. until a viscous liquid is obtained. After the addition of water to a volume of 20.0 ml, dispersion of the mixture by stirring and evaporation of the ethanol under inert atmosphere and under a reduced pressure of 0.4 kPa at a temperature below 30° C., the volume is made up to 20.0 ml by a further addition of water. A milky dispersion is then obtained, which is homogenized until a clear dispersion is obtained. The dispersion is subjected to a sterilizing filtration and then distributed in 2-ml ampoules.

The particle-free composition thereby obtained is frozen. After thawing, a clear dispersion is obtained immediately.

Example 5

The procedure is as above in Example 4, starting from 0.1 g of docetaxel, 1.5 g of Phospholipon 90° and 0.075 g of phosphatidyl glycerol sodium salt. After the addition of water to a volume of 15.0 ml, dispersion of the mixture by stirring and evaporation of the ethanol, the volume is made up to 16.7 ml by a further addition of water. After homogenization, 3.3 ml of an aqueous solution containing 2.0 g of maltose are added. The dispersion obtained is subjected to a sterilizing filtration, then distributed in 2-ml vials and lyophilized.

From the lyophilizate obtained, it is possible to reconstitute a perfectly clear and stable solution after adding 2.0 ml of water containing 0.9% of sodium chloride.

Stability measurements show that the solution is still clear after 8 weeks at a temperature of 20° C.

Example 6

0.87 g of 4α,10β-diacetoxy-2α-benzoyloxy and 5β-20, epoxy-1β-hydroxy-7β,8β-methylene-9-oxo-19-nor-11-taxen-13α-yl (2R,3S)-3'-t-butoxycarbonylamino-2'-hydroxy-3'-phenylpropionate, 17.4 g of Phospholipon 90° and 0.087 g of phosphatidyl glycerol sodium salt are dissolved in 200 ml of ethanol and then stirred until dissolution is complete. The ethanol is evaporated off under an inert atmosphere (nitrogen) and under a reduced pressure of 0.5 kPa at a temperature below 30° C. until an ethanol-free pasty solid is obtained. After the addition of water to a volume of 143.0 ml and dispersion of the mixture by stirring, a dispersion of milky appearance is first obtained, which is homogenized until a clear, fine dispersion is obtained, to which 50 ml of an aqueous solution containing 17.4 g of maltose are added with stirring. The dispersion thereby obtained is subjected to sterilizing filtration using a 0.22 μm filter.

The sterile dispersion is divided into 4.0 ml fractions in 10-ml vials and then lyophilized.

After the lyophilisate has been taken up with 3.5 ml of double-distilled water for injections, a clear, stable solution is obtained immediately.

This solution is stable and clear for more than 8 weeks.

Examples 7 to 25

Using the procedure described in the above examples, analogous compositions are prepared from the derivatives of the taxoid class mentioned below:

4-acetoxy-2α-benzoyloxy-5β20-epoxy-1β,7β,10β-trihydroxy-9-oxo-11-taxen-13α-yl (2R,3S)-3'-t-butoxycarbonylamino-3'-(2-fluorophenyl)-2'-hydroxypropionate;

4-acetoxy-2α-benzoyloxy-5β,20-epoxy-1β,7β,10β-trihydroxy-9-oxo-11-taxen-13α-yl (2R,3S)-3'-butoxycarbonylamino-3'-(4-chlorophenyl)-2'-hydroxypropionate;

4-acetoxy-2α-benzoyloxy-5β,20-epoxy-1β,7β,10β-trihydroxy-9-oxo-11-taxen-13α-yl (2R,3S)-3'-t-butoxycarbonylamino-3'-(4-methoxyphenyl)-2'-hydroxypropionate;

4-acetoxy-2α-benzoyloxy-5β,20-epoxy-1β,7β,10β-trihydroxy-9-oxo-11-taxen-13α-yl (2R,3S)-3'-t-butoxycarbonylamino-3'-(4-fluorophenyl)-2'-hydroxypropionate;

4-actoxy-2α-benzoyloxy-5β,20-epoxy-1β,7β,10β-trihydroxy-9-oxo-11-taxen-13α-yl (2R,3S)-3'-adamantyloxycarbonylamino-2'-hydroxy-3'-phenylpropionate;

4-acetoxy-2α-benzoyloxy-5β,20-epoxy-1β,7β,10β-trihydroxy-9-oxo-11-taxen-13α-yl (2R,3S)-3'-tert-pentyloxycarbonylamino-2'-hydroxy-3'-phenylpropionate;

4-acetoxy-2α-benzoyloxy-5β,20-epoxy-1β,7β,10β-trihydroxy-9-oxo-11-taxen-13α-yl (2R,3S)-3'-(1-methylcyclohexyl)oxycarbonylamino-2'-hydroxy-3'-phenylpropionate;

4-acetoxy-2α-benzoyloxy-5β,20-epoxy-1β,7β,10β-trihydroxy-9-oxo-11-taxen-13α-yl (2R,3S)-3'-(1-methylcyclopropyl)oxycarbonylamino-2'-hydroxy-3'-phenylpropionate;

4-acetoxy-2α-benzoyloxy-5β,20-epoxy-1β,7β,10β-trihydroxy-9-oxo-11-taxen-13α-yl (2R,3S)-3'-(1-methylcyclopenyl)oxycarbonylamino-2'-hydroxy-3'-phenylpropionate;

4-acetoxy-2α-benzoyloxy-5β,20-epoxy-1β,7β,10β-trihydroxy-9-oxo-11-taxen-13α-yl (2R,3S)-3'-(1,1-dimethyl-2-propynyl)oxycarbonylamino-2'-hydroxy-3'-phenylpropionate;

4-acetoxy-2α-benzoyloxy-5β,20-epoxy-1β,7β,9β,10β-tetrahydroxy-11-taxen-13α-yl (2R,3S)-3'-t-butoxycarbonylamino-2'-hydroxy-3'-phenylpropionate;

4-acetoxy-2α-benzoyloxy-5β,20-epoxy-1β,7β-dihydroxy-9-oxo-11-taxen-13α-yl (2R,3S)-3'-t-butoxycarbonylamino-2'-hydroxy-3'-phenylpropionate;

4-acetoxy-2α-benzoyloxy-5β,20-epoxy-1β,7β,10β-trihydroxy-9-oxo-11-taxen-13α-yl (2R,3S)-3'-t-butoxycarbonylamino-2'-hydroxy-3'-(2-thienyl)propionate;

4-acetoxy-2α-benzoyloxy-5β,20-epoxy-1β,7β,10β-trihydroxy-9-oxo-11-taxen-13α-yl (2R,3S)-3'-t-butoxycarbonylamino-3'-(2-furyl)-2'-hydroxypropionate;

4-acetoxy-2α-benzoyloxy-5β,20-epoxy-1β,7β,10β-trihydroxy-9-oxo-11-taxen-13α-yl (2R,3S)-3'-t-butoxycarbonylamino-2'-hydroxy-3'-(3-thienyl)propionate;

4-acetoxy-2α-benzoyloxy-5β,20-epoxy-1β,10β-dihydroxy-9-oxo-11-taxen-13α-yl (2R,3S)-3'-t-butoxycarbonylamino-2'-hydroxy-3'-phenylpropionate;

4-acetoxy-2α-benzoyloxy-5β,20-epoxy-1β,7β-dihydroxy-9,10-dioxo-11-taxen-13α-yl (2R,3S)-3'-t-butoxycarbonylamino-2'-hydroxy-3'-phenylpropionate;

4-acetoxy-2α-benzoyloxy-5β,20-epoxy-1β-hydroxy-9-oxo-11-taxen-13α-yl (2R,3S)-3'-t-butoxycarbonylamino-2'-hydroxy-3'-phenylpropionate;

4-acetoxy-2α-benzoyloxy-5β20-epoxy-1β,10β-dihydroxy-7β,8β-methylene-9-oxo-19-nor-11-taxen-13α-yl (2R,3S)-3'-t-butoxycarbonylamino-2'-hydroxy-3'-phenylpropionate.

Example of Preparation of a Derivative of General Formula (I)

76 mg of sodium hydrogen carbonate are added to a solution, maintained under an argon atmosphere, of 550 mg of 4α,10β-diacetoxy-2α-benzoyloxy-5β,20-epoxy-1β-hydroxy-7β,8β-methylene-9oxo-19-nor-11-taxen-13α-yl (2R,3S)-3-amino-2-hydroxy-3-phenylpropionate in 1 cm³ of dichloromethane, and a solution of 197 mg of di-tert-butyl dicarbonate in 1 cm³ of dichloromethane is then added dropwise at a temperature in the region of 20° C. The solution obtained is stirred for 15 hours at a temperature in the region of 20° C., and a mixture of 5 cm³ of distilled water and 10 cm³ of dichloromethane is then added to it. The aqueous phase is extracted with 5 cm³ of dichloromethane.

The combined organic phases are dried over magnesium sulphate, filtered and then concentrated to dryness under reduced pressure (2.7 kPa) at 40° C. 780 mg of a white foam are thereby obtained, which foam is purified by chromatography at atmospheric pressure on 50 g of silica (0.063–0.2 mm) contained in a column 2.5 cm in diameter, eluting with a methanol/dichloromethane (1:99, then 2.5:97.5 by volume) mixture, collecting 10-cm³ fractions. The fractions containing only the desired product are pooled and concentrated to dryness under reduced pressure (2.7 kPa) at 40° C. 660 mg of a white foam are thereby obtained. A sample of 300 mg is purified by preparative chromatography on 12 thin-layer silica plates (Merck Silica gel 60F$_{254}$; thickness 0.25 mm), eluting with a methanol/dichloromethane (4:96 by volume) mixture. After elution of the zone corresponding to the main product with a methanol/dichloromethane (10:90 by volume) mixture, followed by evaporation of the solvents under reduced pressure (0.27 kPa) at a temperature in the region of 40° C., 159.7 mg of 4α,10β-diacetoxy-2α-benzoyloxy-5β,20-epoxy-1β-hydroxy-7β,8β-methylene-9-oxo-19-nor-11-taxen-13α-yl (2R,3S)-3-tert-butoxycarbonylamino-2-hydroxy-3-phenylpropionate are obtained in the form of a white foam, the characteristics of which are as follows:

optical rotation: $[\alpha]_D^{20} = -34°$ (c=0.565; methanol)

proton NMR spectrum: (400 MHz; CDCl$_3$; δ in ppm; coupling constants J in Hz): 1.28 (s, 3H: —CH$_3$ 16 or 17); 1.30 (s, 9H: —C(CH$_3$)$_3$); 1.38 (mt, 1H: —H 7); 1.60 )s, 3H: —CH$_3$ 16 or 17); 1.68 and 2.25 (t and m, 1H each: CH$_3$ of the cyclopropane); 1.85 (s, 3H: —CH$_3$ 18); 2.10 and 2.45 (d and td, 1H each: —CH$_3$— at position 6); 2.23 (s, 3H: —COCH$_3$ at position 10); 2.22 and 2.40 (m, 1H each: —CH$_3$— at position 14); 2.40 (s, 3H: —COCH$_3$ at position 4); 3.28 (d, 1H: —OH at position 2'); 4.05 and 4.22 (d, 1H each: —CH$_2$— at position 20); 4.10 (d, 1H: —H 3); 4.62 (broad s, 1H: —H 2'); 4.73 (d, 1H: —H 5); 5.29 (broad d, 1H: —H 3'); 5.37 (d, 1H: —CPNH—); 5.67 (d, 1H: —H at position 2); 6.28 (broad, t, 1H: —H 13); 6.33 (s, 1H: —H 10); from 7.30 to 7.45 (mt, 5H: —C$_4$H$_5$ at position 3'); 7.51 [t, 2H: —OCOC$_6$H$_5$ (—H 3 and —H 5)]; 7.61 [t, 1H: —OCOC$_6$H$_5$ (—H 4)];8.17 [d, 2H: —OCOC$_6$H$_5$ (—H 2 and —H 6)].

Starting from 1.6 g of 4α,10β-diacetoxy-2α-benzoyloxy-5β,20-epoxy-1β-hydroxy-7β,8β-methylene-9-oxo-19-nor-11-taxen-13α-yl (4S,5R)-3-tert-butoxycarbonyl-2,2-dimethyl-4-phenyl-5-oxazolidine-carboxylate, 1.14 g of 4α,10β-diacetoxy-2α-benzoyloxy-5β,20-epoxy-1β-hydroxy-7β,8β-methylene-9-oxo-19-nor-11-taxen-13α-yl (2R,3S)-3-amino-2-hydroxy-3-phenylpropionate are obtained in the form of a white foam.

Starting from 2.2 g of 4,α,10β-diacetoxy-2α-benzoyloxy-5β,20-epoxy-1β-hydroxy-9-oxo-7β-trifluoromethanesulphonate-11-taxen-13α-yl (4S,5R)-3-tert-butoxycarbonyl-2,2-dimethyl-4-phenyl-5-oxazolidinecarboxylate, 1.62 g of 4α,10β-diacetoxy-2α-benzoyloxy-5β,20-epoxy-1β-hydroxy-7β,8β-methylene-9-oxo-19-nor-11-taxen-13α-yl (4S,5R)-3-tert-butoxycarbonyl-2,2-dimethyl-4-phenyl-5-oxazolidinecarboxylate are obtained in the form of a white foam.

Starting from 2.4 g of 4α,10β-diacetoxy-2α-benzoyloxy-5β,20-epoxy-1β,7β-dihydroxy-9-oxo-11-taxen-13α-yl (4S,5R)-3-tert-butoxycarbonyl-2,2-dimethyl-4-phenyl-5-oxazolidinecarboxylate, 2.46 g of 4α,10β-diacetoxy-2α-benzoyloxy-5β,20-epoxy-1β-hydroxy-9-oxo-7β-trifluoromethanesulphonate-11-taxen-13α-yl (4S,5R)-3-tert-butoxycarbonyl-2,2-dimethyl-4-phenyl-5-oxazolidinecarboxylate are obtained in the form of a white foam.

4α,10β-Diacetoxy-2α-benzoyloxy-5β,20-epoxy-1β,7β-dihydroxy-9-oxo-11-taxen-13α-yl (4S,5R)-3-tert-butoxycarbonyl-2,2-dimethyl-4-phenyl-5-oxazolidinecarboxylate is obtained under the conditions described in International publication WO 92/09589.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Pharmaceutical composition comprising,
    as active principle, docetaxel or a taxoid derived from docetaxel,
    at least one unsaturated phospholipid and
    at least one negative phospholipid, said at least one negative phospholipid being different from said at least one unsaturated phospholipid.

2. Pharmaceutical composition according to claim 1, wherein comprises 3 to 15 mg/ml of active principle.

3. Pharmaceutical composition according to claim 1 (or 2), wherein the active principle is of formula:

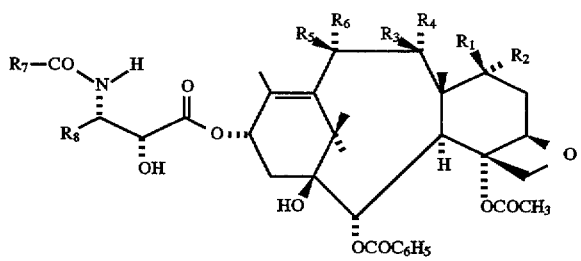

in which:

R$_1$ and R$_2$ each represent a hydrogen atom, optionally one of R$_1$ and R$_2$ represents a hydrogen atom and the other represents a hydroxyl, acyloxy or acylcarbonyloxy radical, optionally R$_2$ represents a hydrogen atom and R$_1$ form a bond with the carbon atom of the methyl radical at the α-position to form a cyclopropane ring, one of R$_3$ and R$_4$ represents a hydrogen atom and the other represents a hydroxyl radical, optionally R$_3$ and R$_4$ together form an oxo radical, R$_5$ and R$_6$ each represent a hydrogen atom, optionally one of R$_5$ and R$_6$ represents a hydrogen atom and the other represents a hydroxyl, acyloxy, acylcarbonyloxy or alkoxymethylcarbonyloxy radical, optionally R$_5$ and R$_6$ together form an oxo radical, R$_7$ represents an alkoxy, alkenyloxy or cycloalkyloxy radical, and R$_8$ represents an alkyl, straight or branched-chain alkenyl or alkynyl radical or a cycloalkyl radical containing 3 to 6 carbon atoms, or alternatively R$_8$ represents a phenyl radical unsubstituted or substituted with at least one or more identical or different atoms or radicals selected from halogen atoms and alkyl, alkoxy, dialkylamino, acylamino, alkoxycarbonylamino and trifluoromethyl radicals, or a 5-membered aromatic heterocyclic radical containing at least one identical or different hetero atoms selected from nitrogen, oxygen and sulphur atoms, the alkyl radicals and the alkyl portions of other radicals containing 1 to 8 carbon atoms in a straight or branched-chain, and the alkenyl or alkynyl radicals containing 2 to 8 carbon atoms.

4. Pharmaceutical composition according to claim 3, wherein $R_2$ represents a hydrogen atom, $R_1$ represents a hydrogen atom or a hydroxyl radical, or optionally $R_1$ forms a single bond with the carbon atom of the methyl radical at the α-position and $R_2$ represents a hydrogen atom, $R_3$ and $R_4$ together form an oxo radical, $R_5$ represents a hydrogen atom and $R_6$ represents a hydrogen atom or a hydroxyl, acetyloxy or methoxyacetyloxy radical, optionally $R_5$ and $R_6$ together form an oxo radical, $R_7$ represents a t-butoxy radical and $R_8$ represents an isobutyl, isobutenyl, butenyl, cyclohexyl, phenyl,2-furyl, 3-furyl, 2-thienyl, 3-thienyl, 2-thiazolyl, 4-thiazolyl or 5-thiazolyl radical.

5. Pharmaceutical composition according to claim 4, wherein the active principle is docetaxel.

6. Pharmaceutical composition according to claim 4, wherein the active principle is 4α,10β-diacetoxy-2α-benzoyloxy-5β,20-epoxy-1β-hydroxy-7 β,8β-methylene-9-oxo-19-nor-11-taxen-13α-yl (2R,3S)-3'-t-butoxycarbonylamino-2'-hydroxy-3'-phenylpropionate.

7. Pharmaceutical composition according to claim 1, wherein the concentration of active principle ranges from 5 to 15 mg/ml.

8. Pharmaceutical composition according to claim 1, wherein the unsaturated phospholipid is a natural, synthetic or semi-synthetic phospholipid.

9. Pharmaceutical composition according to claim 8, wherein the unsaturated phospholipid is a natural phospholipid.

10. Pharmaceutical composition according to claim 9, wherein the natural phospholipid is a phospholipid of vegetable origin.

11. Pharmaceutical composition according to claim 1, wherein the unsaturated phospholipid comprises 70 to 100% of phosphatidylcholine.

12. Pharmaceutical composition according to claim 10, wherein the natural phospholipid of vegetable origin contains a level of unsaturated acyl chains of greater than 70%.

13. Pharmaceutical composition according to claim 1, wherein the active principle is present in a proportion of 1 to 30% by weight relative to the total weight of the phospholipids.

14. Pharmaceutical composition according to claim 13, wherein the active principle is present in a proportion of 3 to 20% by weight relative to the total weight of phospholipids.

15. Pharmaceutical composition according to claim 14, wherein the active principle is present in a proportion of 3.5 to 10% by weight relative to the total weight of phospholipids.

16. Pharmaceutical composition according to claim 1, wherein the negative Phospholipid is selected from the alkali metal salts or quaternary ammonium salts of phosphatidylglycerol, phosphatidylserine, phosphatidylinositol or phosphatidic acid, or of a derivative thereof.

17. Pharmaceutical composition according to claim 16, wherein the negative Phospholipid is present in a proportion of 0.1 to 4% by weight relative to the total weight of unsaturated Phospholipid.

18. Pharmaceutical composition according to claim 17, wherein the negative Phospholipid is present in a proportion of 0.4 to 0.8% by weight relative to the total weight unsaturated phospholipid(s).

19. Pharmaceutical composition according to claim 18, wherein the negative Phospholipid is present in a proportion of 0.5% by weight relative to the total amount of unsaturated Phospholipid.

20. Pharmaceutical composition according to claim 1, which is in liquid, frozen or lyophilized form.

21. Pharmaceutical composition according to claim 1, further comprising a cryoprotective agent and/or a isotonicity adjusting agent.

22. Pharmaceutical composition according to claim 21, wherein the agent is selected from sugars, polymers and amino acids.

23. Pharmaceutical composition according to claim 1, in the form of a solution or dispersion comprises particles containing active principle having on average a diameter of less than 200 nm.

24. Pharmaceutical composition according to claim 23, wherein the solution or dispersion comprises particles containing active principle having on average a diameter less than 100 nm.

25. A process for preparing a pharmaceutical composition as defined in claim 1, which comprises forming a homogeneous dispersion by dissolving in an alcohol at least one unsaturated phospholipid, a small amount of at least one negative phospholipid, said at least one negative phospholipid being different from said at least one unsaturated phospholipid, and an active principle which is docetaxel or a taxoid derived from docetaxel, evaporating all or part of the alcohol until a gel or a viscous liquid is obtained, taking up the gel or viscous liquid by adding water with stirring and then homogenizing, and then optionally freezing or lyophilizing the dispersion obtained.

26. A process according to claim 25, wherein the alcohol is ethanol.

27. Process according to claim 25, wherein the dispersion obtained is subjected to sterilizing filtration.

28. Method comprising preparation of a ready-to-use, stabilized injectable solution utilizing a frozen or lyophilized composition as defined in claim 20.

29. Method of preventing or inhibiting tumor growth comprising the step of administering to a patient in need thereof an amount of a pharmaceutical composition as defined in claim 1 effective for said prevention or inhibition of tumor growth.

30. A pharmaceutical composition according to claim 1, wherein the negative phospholipid is present in a proportion of 0.1 to 4% by weight relative to the total weight of unsaturated phospholipids.

31. A pharmaceutical composition according to claim 30, wherein the negative phospholipid is present in a proportion of 0.4 to 0.8% by weight relative to the total weight of unsaturated phospholipids.

32. A pharmaceutical composition according to claim 31, wherein the negative phospholipid is present in a proportion of 0.5% by weight relative to the total weight of unsaturated phospholipids.

33. A pharmaceutical composition according to claim 10, wherein the phospholipid of vegatative origin is of sunflower or of soya bean origin.

* * * * *